United States Patent [19]
Coleman

[11] Patent Number: 5,307,595
[45] Date of Patent: May 3, 1994

[54] METHOD OF SHARPENING TWEEZERS

[76] Inventor: Kenneth J. Coleman, 6217 Lou St., Crystal Lake, Ill. 60014

[21] Appl. No.: 58,948

[22] Filed: May 7, 1993

Related U.S. Application Data

[62] Division of Ser. No. 871,475, Apr. 21, 1992, Pat. No. 5,263,754.

[51] Int. Cl.⁵ .............................................. B24B 1/00
[52] U.S. Cl. ................................. 51/328; 51/145 R; 51/144; 51/216 T
[58] Field of Search ............... 51/144, 145 R, 216 T, 51/217 T, 218 T, 236, 237 R, 281 R, 328

[56] References Cited

U.S. PATENT DOCUMENTS

| | | | |
|---|---|---|---|
| 291,235 | 1/1884 | Sibley | 51/145 R |
| 763,743 | 6/1904 | Ensign | 51/145 R |
| 3,668,814 | 6/1972 | Freerks | 51/144 |

*Primary Examiner*—Jack Lavinder
*Attorney, Agent, or Firm*—Mathew R. P. Perrone, Jr.

[57] ABSTRACT

Tweezers have two arms mounted on a spacer with a barbed tip at the other end of the arms. The tweezers are sharpened to the barbed tip with a belt sanding apparatus, which includes a holding device for positioning the tweezers on the belt sanding apparatus. A magnifying lens may be mounted on the spacer and positioned over the barbed tip to assist in sighting the foreign object to be removed.

1 Claim, 4 Drawing Sheets

METHOD OF SHARPENING TWEEZERS

This application is a divisional of application Ser. No. 07/871475, filed Apr. 21, 1992, now U.S. Pat. No. 5,263,754.

This invention relates to tweezers and a method and apparatus for sharpening the tweezers to a barbed point, and more particularly to a pointed tweezers and a method and apparatus for sharpening the same to a barbed point capable of cutting through a surface layer of skin to retrieve a foreign object. A magnifying glass may also be included on the tweezers to assist in viewing the area being accessed by the tweezers.

BACKGROUND OF THE INVENTION

Tweezers are well known in the art. Tweezers are generally used for health or cosmetic purposes. The health reasons generally relate to removing a foreign object from the skin. The cosmetic reasons relate to personal appearance.

One of the standard uses for a pair of tweezers is to remove a splinter or other foreign object from the skin. A typical foreign object is a small piece of foreign material not naturally found in the body. A wood splinter is a common foreign object. But unless the splinter protrudes from the skin, it is difficult, if not impossible, to use prior art tweezers to remove the splinter. It is extremely useful if tweezers can be used to remove a splinter from the skin, when the splinter does not protrude from the skin.

It is also desirable to use tweezers to remove hair. Basically, tweezers used for removing hair lose their strength and require a straight on angle to grip the hair and pull it out, as desired. Such pulling and gripping is uncomfortable and inconvenient. If a suitable means with an appropriate tweezers can be used to grip the hair, a great advantage can result.

Standard tipped tweezers are generally flat and cannot be used for close gripping. It is desirable to provide more efficient gripping in order to achieve the desired removal. It is thus desired to modify the tip of the tweezers and achieve more efficient gripping.

The difficulty of removing a foreign object from the skin is well known. When a foreign object gets even slightly embedded under the skin, it is very difficult to remove the same. It is common to use needles or pins or similar devices, which penetrate the skin layers over the foreign object. However, the most effective device to use for such procedures is tweezers.

Standard tweezers do not permit gripping of a foreign object, which is at least partially under the skin. So it is, therefore, necessary to make access to the splinter or other foreign object under the skin with a pin or needle. If tweezers can be developed to cut through the skin without damaging the skin beneath the foreign object and grip the foreign object, great advantages are obtained.

It is difficult to grip and remove a foreign object from human flesh because of the usually embedded nature of the object. With the embedded foreign object, it is extremely difficult to reach and remove the object. Presently available tweezers cannot both cut through the skin and grip the object in a suitable fashion for removal.

Many different types of sharpened tweezers are known for attempting to remove embedded materials. However, these tweezers suffer from gross inefficiency in that the sharpening for enhanced gripping the detracts from the cutting capability. It is highly desirable to provide a sharpening device which will permit both cutting and gripping and cutting for removal of a foreign object from the skin. Such a sharpening device can be very complicated. No sharpening device is known to efficiently achieve these desired results. However, it is highly desired to achieve these desired results in as efficient a fashion as possible.

It is very difficult to provide this cutting and gripping tip on tweezers. There is no uniform way of making this desired tweezers with this tip and no simplified method of achieving the same.

Many different ways are known to attach the two arms of the tweezers at one end. It is extremely difficult to accomplish this in an efficient fashion while at the same time retaining the desired flexibility and function. If the ease of attachment can be provided while retaining the desired flexibility and function, our desired results can be achieved.

Another difficulty in removing foreign objects from the skin is the inability of a person to see the object. To remove the object, the object must be seen before it can be removed. The small size of some of these foreign particles that do get embedded in the skin render them difficult to both see and remove from the skin. Accordingly, improved sight to simplify removal of a foreign object is highly desired.

SUMMARY OF THE INVENTION

Accordingly among the many objectives of the present invention is to provide an improved pair of tweezers capable of gripping hair, a splinter, or another object more efficiently.

It is a further objective of this invention to provide tweezers having a sharpened gripping point.

A still further objective of this invention is to provide tweezers having greater durability.

Yet a further objective of this invention is to provide tweezers having greater strength.

Another objective of this invention is to provide tweezers for removing a hair.

Yet another objective of this invention is to provide tweezers for removing a splinter.

Still another objective of this invention is to provide tweezers with a barbed tip.

It is a further objective of this invention to provide an apparatus for providing a barbed tip on tweezers.

A still further objective of this invention to provide an apparatus, with a consistent holding device, for providing a barbed tip on tweezers.

Yet a further objective of this invention to provide an apparatus, with a consistent sharpening device, for providing a barbed tip on tweezers.

These and other objectives of the invention (which other objectives become completely clear by considering the specifications, claims and drawings as a whole) are met by providing tweezers having with a barbed tip. Tweezers are sharpened with a belt sanding apparatus, which includes a holding device for positioning the tweezers on the belt sanding apparatus. A magnifying lens, which may be positioned over the barbed tip to assist in sighting the foreign objective, is also available.

BRIEF DESCRIPTION OF DRAWINGS

Throughout the figures of the drawings, where the same part appears in more than one figure, the same number is applied thereto.

DESCRIPTION OF THE PREFERRED EMBODIMENTS

The tweezers of this invention include a first arm mounted parallel to a second arm. Between the arms at the fixed end of each arm is a spacing device. Each arm is secured to the spacing device. Each arm may be riveted on an opposite side of the spacing device. If desired, a magnifying glass or a similar device to aid in visualizing the foreign object to be removed may provided as well, engaged in a pivotal fashion to the spacing device.

In order to achieve the desired barbed pointed end of the tweezers capable of both cutting into the skin without causing bleeding or similar problems ad gripping a foreign object, the sharpening device includes a tool holder capable of receiving both arms of the tweezers simultaneously. The tool holder holds the tips together for sharpening and creating the barbed end.

The tool holder has a bearing mounted hollow cylinder. Through the bearing mounted hollow cylinder or sleeve fits the gripping end of the tweezers and squeezes the points together. The points at the gripping end are then sharpened on the belt and thereby achieve the burr end or barbed end to permit gripping and removing of the foreign object in the skin.

The points of the tweezers are then placed on a belt sander at an appropriate empirical position such that the barbed end is produced. In this fashion, an efficient method of producing the pointed and barbed end is achieved.

It is also feasible to mount a magnifying glass on the cylindrical spacer, to which the arms are riveted, to assist in sighting of the foreign object. The magnifying glass includes an arm attached to the glass portion with a circular member, the arm clipping around the cylindrical spacer. This clipping mechanism permits an efficient functioning of the tweezers.

Figure 1:
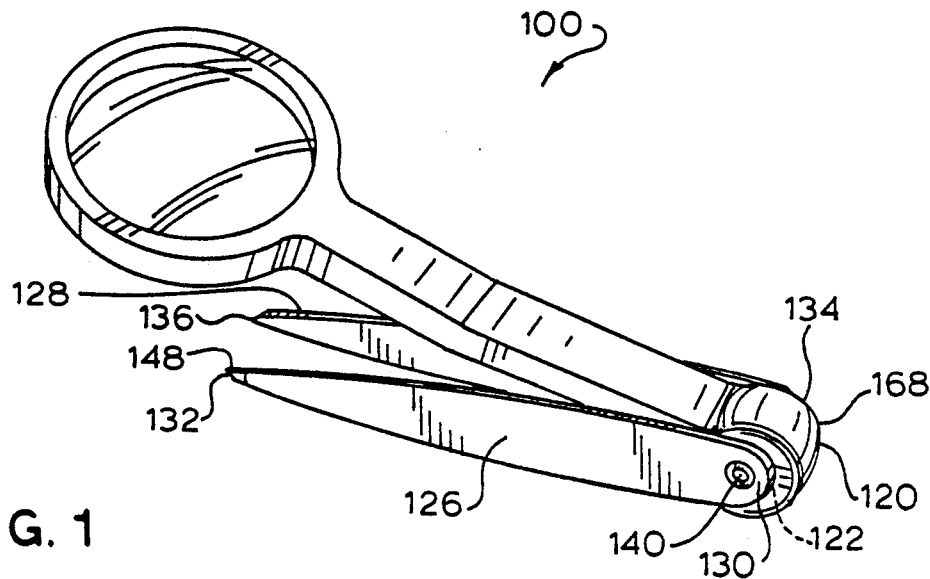
FIG. 1 depicts a perspective view of the tweezers 100 with magnifying glass 160 of this invention.
Figure 2:
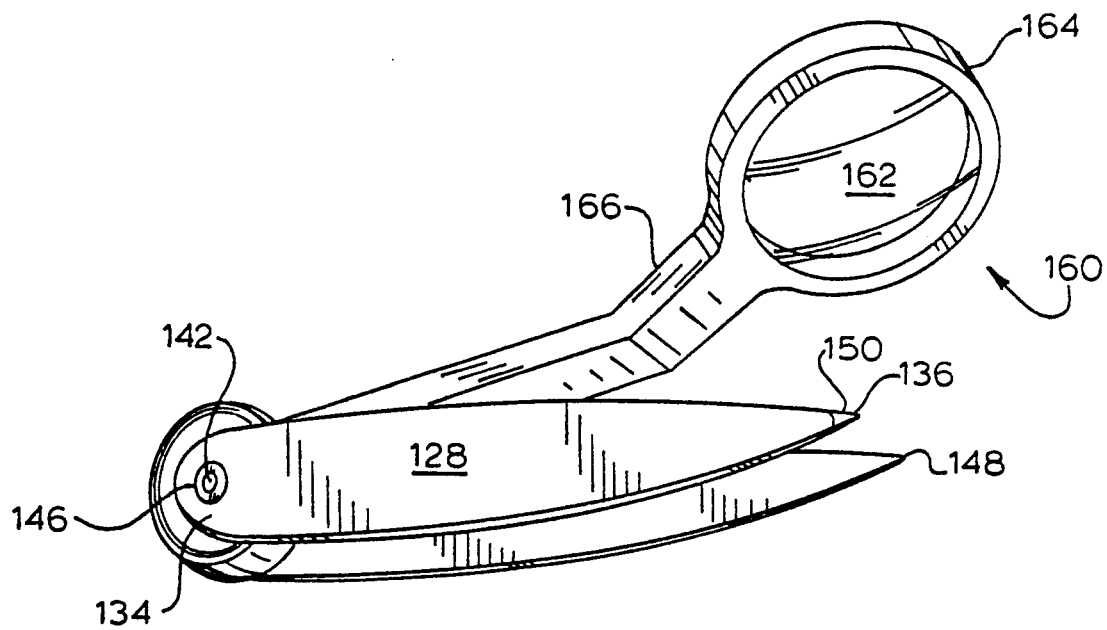
FIG. 2 depicts a perspective view of the tweezers 100 of this invention, showing a perspective opposite to that of FIG. 1.

Referring now to FIG. 1 and FIG. 2, opposite perspective views of the splinter pulling tweezers 100 are depicted. The splinter pulling tweezers 100 have a base 120 with a first arm 126 and a second arm 128 extending therefrom. First arm 126 and second arm 128 are substantially perpendicular to the axis of base 120 and parallel to each other. Preferably, base 120 is cylindrical in nature with an axial base aperture 122 therethrough.

Figure 3:
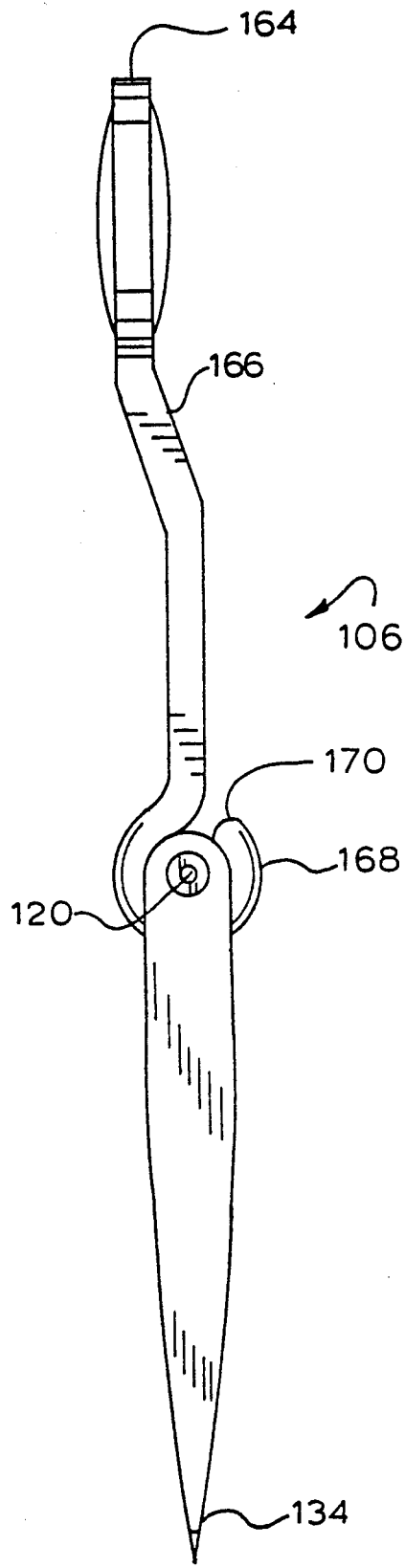
FIG. 3 depicts a linearly extended, side view of the tweezers 100 with magnifying glass 160 of this invention.

Both first arm 126 and second arm 128 are elongated as shown in FIG. 3, and formed of flat pieces of relatively rigid, but springlike, metal substantially symmetrical to each other. First arm 126 has a first rounded end 130 secured to base 120 and a first tapered end 132 oppositely disposed from the first rounded end 130. Likewise, second arm 128 has a second rounded end 134 secured to base 120 and a second tapered end 136 oppositely disposed from the second rounded end 134.

Within first rounded end 130 is first rounded end aperture 140. Likewise, second rounded end 136 has a second rounded end aperture 142. First rounded end aperture 140 and second rounded end aperture 142 line up on opposite ends of base aperture 122 and receive rivet 146 therethrough, thereby forming the tweezers 100.

First arm 126 extends from first rounded end 130 down to and terminates in a first splinter point 148. Likewise, second arm 128 extends from second rounded end 134 down to and terminates in a second splinter point 150.

Also a magnifying glass 160 is optionally and preferably mounted on the tweezers 100. The magnifying glass 160 includes a magnifying lens 162 secured at a lens end 164 of magnifying arm 166. Magnifying arm 166 is of sufficient length to allow lens end 164 and thus magnifying lens 162 to be positioned over first splinter point 148 and second splinter point 150.

Oppositely disposed from lens end 164 of magnifying arm 166 is clip end 168. Clip end 168 includes a flexible arcuate base clip 170 to removably and rotatbly fasten magnifying arm 166 to base 120.

Figure 4:
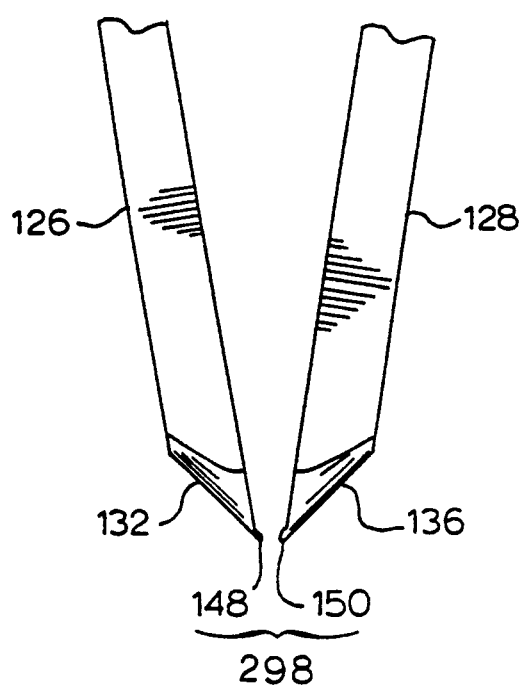
FIG. 4 depicts a magnified view of splinter engaging points 298 of the tweezers 100 of this invention.

The splinter points 148 and 150 are more clearly shown in FIG. 4, wherein first tapered end 132 and second tapered end 136 are shown in a magnified form to emphasize a barbed nature thereof. First splinter point 148 and second splinter point 150 are created by engaging first tapered end 132 against second tapered end 136, inserting the engaged tapered ends 132 and 136 in the tweezer holding mechanism 350 which maintains the ends 132 and 136 engaged, applying the engaged ends to the belt 302 in a manner tangentially thereto, and rotating the engaged ends 132 and 136 about their longitudinal axis on belt 302 to form a tapered point thereon. In this manner first splinter point 148 and second splinter point 150 are formed in a barbed fashion, to provide a splinter puller on tweezer 100. By splinter puller, it is meant a device to remove a splinter or other foreign body from the skin.

This manner of sharpening produces a sharpened pencil-like appearance when first arm 126 and second arm 128 are held together. First point 148 and second point 150 form a pencil type point, which is tapered with the extreme end edge of each point 148 and 150 being sharpened so that the tweezers 100 may cut into skin and extract the splinter or other foreign object. Preferably, the sharpened points 148 and 150, when pressed together, generally form a cone, having a conical vertex at the extreme end edge thereof.

The base angle of the cone taken across the base of the cone may vary within certain ranges. Preferably the angle of the cone is up to about eighty (80°) degrees. More preferably the angle of the cone is up to about seventy (70°) degrees. Most preferably the angle of the cone 160 is about forty five (45°) degrees to sixty five (65°) degrees.

Figure 5:
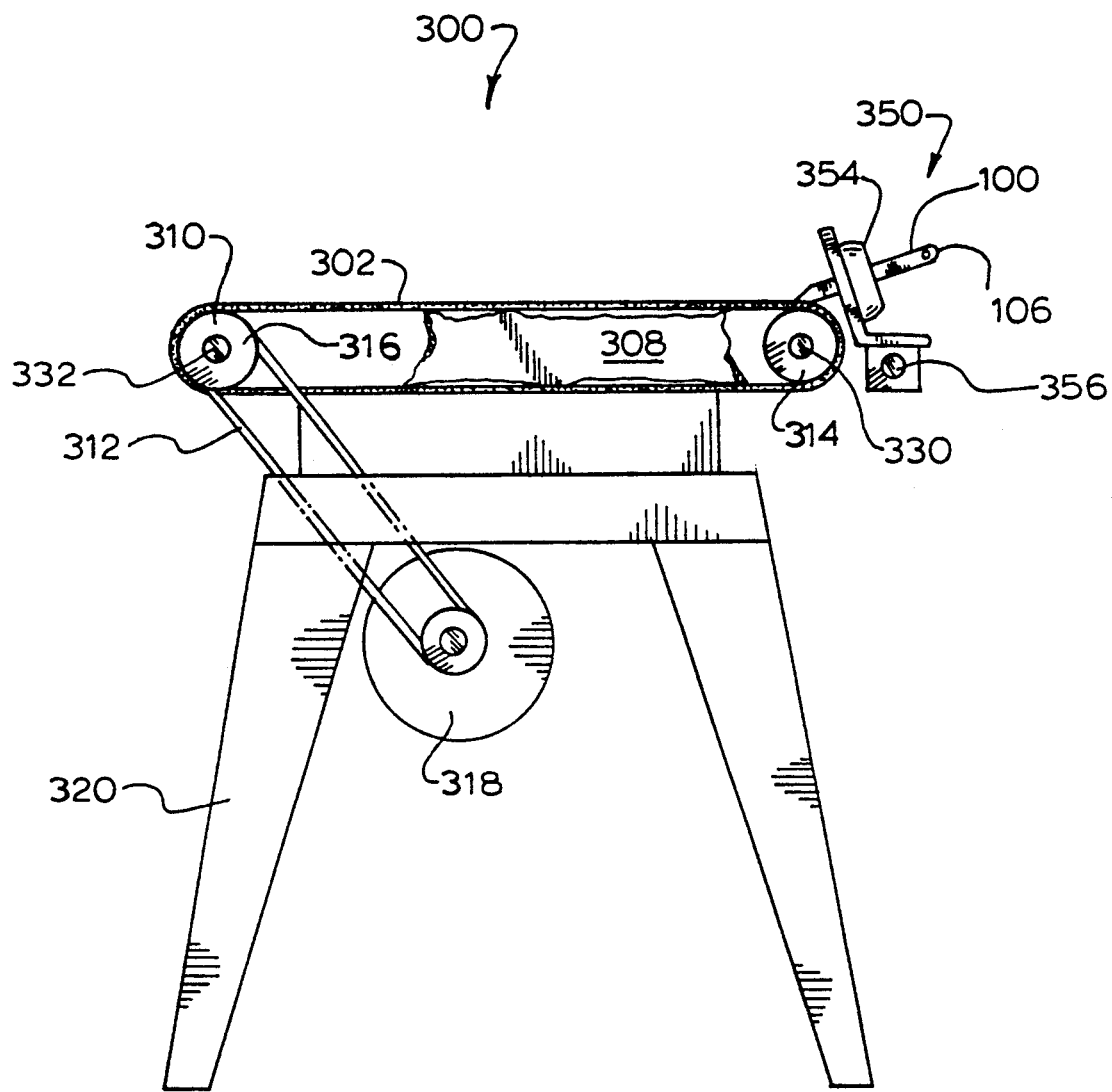
FIG. 5 depicts a side view of the sharpening device 300 for tweezers 100 of this invention.

Referring now to FIG. 5, a belt grinding device 300 achieves the barbed tip on the tweezers 100. The grinding device 300 includes a belt housing 310 in working cooperation with tweezers holding mechanism 350. The tweezers holding mechanism 350 is movable in relation to the belt housing 308, so that the first splinter point 148 and second splinter point 150 may be formed efficiently.

Within the belt housing 308 is included the grinding belt 302 and a roller assembly 310 for engaging the grinding belt 302. Roller assembly 310 includes a first roller 314 mounted on a first post 330 and a second roller 316 mounted on a second post 332. Grinding belt 302 is preferably continuous, and first roller 314 is spaced a predetermined distance from second roller 316, to maintain grinding belt 302 taut thereabout. The driving belt 312 causes the grinding belt 302 to be driven by an electric motor 318 attached in a standard fashion to one or both rollers.

Figure 6:
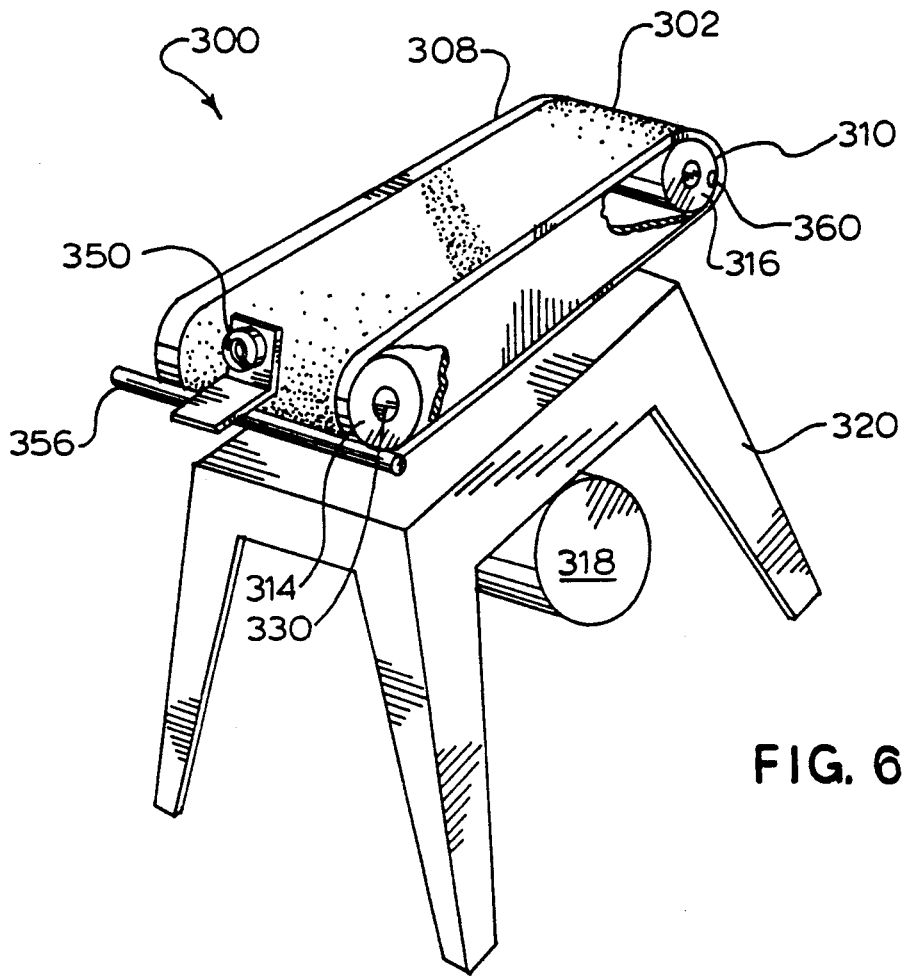
FIG. 6 depicts a perspective view of the sharpening device 300 for tweezers 100 of this invention.

When considering FIG. 5 and FIG. 6, the electric motor 318 is actuated to drive the grinding belt 302 at an appropriate speed and for an appropriate duration. A stand 320 supports the roller assembly 310 and the electric motor 318 while providing for a fastener 360 to install or remove the grinding belt 302 and position the belt grinder 310 on the roller assembly 310. In this fashion, the efficient sharpening can be achieved.

Figure 7:
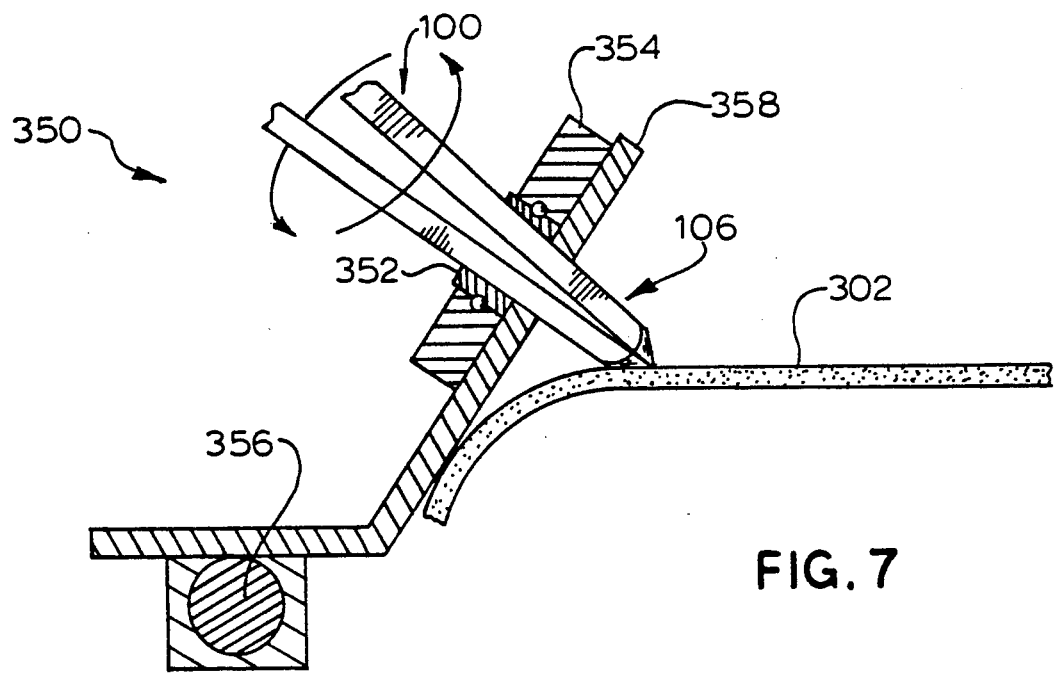
FIG. 7 depicts a side, partially cross-sectional view of the tweezer holding mechanism 350 for sharpening device 300 of this invention.

Now considering FIG. 5 and FIG. 7, the grinding belt 302 has a sharpening side suitable for sharpening the tweezers 100. Mounted adjacent to one end of the belt 302, is the tweezers holding mechanism 350 having a rotatable sleeve 352 for holding the tweezers 100 therein. Through the rotatable sleeve 352 is inserted the tweezers 100. Sleeve housing 354 slides along a bar 356 mounted on stand 320, thereby allowing use of the entire width of grinding belt 302 for sharpening. Sleeve support 358 connects sleeve housing 354 to bar 356. Tweezers 100 are rotated within rotatable sleeve 352 while in contact with the grinding belt 302 to achieve the barbed tip.

Rotatable sleeve 352 is mounted in sleeve housing 354. Preferably, rotatable sleeve 352 is bearing supported (as shown in in FIG. 7) when mounted in sleeve housing 354. Such bearing support may be accomplished in any suitable fashion.

This application—taken as a whole with the specification, claims, abstract, and drawings—provides sufficient information for a person having ordinary skill in the art to practice the invention disclosed and claimed herein. Any measures necessary to practice this invention are well within the skill of a person having ordinary skill in this art after that person has made a careful study of this disclosure.

Because of this disclosure and solely because of this disclosure, modification of this method and apparatus can become clear to a person having ordinary skill in this particular art. Such modifications are clearly covered by this disclosure.

What is claimed and sought to be protected by Letters Patent of the United States is:

1. A method of sharpening tweezers to have a barbed tip, wherein said method comprises:
    a) securing a rounded end of a first arm and a second arm to a spacer means to form said tweezers;
    b) abutting an opposing end of said first arm to an opposing end of said second arm to form abutted ends;
    c) inserting said abutted ends into a rotatable sleeve mounted in a sleeve housing;
    d) applying said abutted ends to an endless moving belt; and
    e) rotating said abutted ends on said endless moving belt to sharpen said abutted ends of said tweezers and form said barbed tip.

* * * * *